United States Patent [19]

Zadini et al.

[11] Patent Number: 5,527,291
[45] Date of Patent: Jun. 18, 1996

[54] MANUAL CATHETER PLACEMENT DEVICE

[76] Inventors: Filiberto P. Zadini, 16814 Rayden St., North Hills, Calif. 91343; Giorgio C. Zadini, 2237 Hilltop La., Camarillo, Calif. 93012

[21] Appl. No.: 249,161

[22] Filed: May 24, 1994

[51] Int. Cl.$^6$ .................................................. A61M 5/178
[52] U.S. Cl. ............................................ 604/165; 604/158
[58] Field of Search .................................... 604/156, 158, 604/159, 165, 169

[56] References Cited

U.S. PATENT DOCUMENTS

| | | | |
|---|---|---|---|
| 2,626,604 | 1/1953 | Nadeau | 604/156 |
| 2,679,843 | 6/1954 | May | 604/156 |
| 3,487,834 | 1/1970 | Smith, Jr. et al. | 604/165 |
| 3,572,334 | 3/1971 | Petterson | 604/159 |
| 3,792,703 | 2/1974 | Moorehead | 604/158 |
| 4,292,970 | 10/1981 | Hession, Jr. | 604/158 |
| 4,311,138 | 1/1982 | Sugarman | 604/165 |
| 4,488,545 | 12/1984 | Shen | 604/165 |
| 4,601,710 | 7/1986 | Moll | 604/165 |
| 5,019,049 | 5/1991 | Haining | 604/165 |
| 5,104,382 | 4/1992 | Brinkerhoff et al. | 60/165 |
| 5,158,552 | 10/1992 | Borgia et al. | 604/165 |
| 5,312,354 | 5/1994 | Allen et al. | 604/156 |
| 5,312,361 | 5/1994 | Zadini et al. | 604/165 |

*Primary Examiner*—Paul J. Hirsch
*Attorney, Agent, or Firm*—Palmatier, Sjoquist & Helget

[57] ABSTRACT

An improved manual catheter placement device to facilitate successful cannulation by minimizing risks of needle tip disengagement with a penetrated blood vessel and by minimizing risks of blood vessels overpenetration. The device comprises a needle, a catheter concentric with the needle, means of manually creating vacuum to accelerate backflow of blood upon occurred penetration, means for manually advancing the catheter, said means for manually advancing the catheter being actuated by said means for creating the vacuum. Actuation of said means for catheter advancement may be either achieved by release of said means for catheter advancement, said advancing means being positioned within easy reach of the operator's hand which creates the vacuum, so that no repositioning of the vacuum creating hand nor a two hands operation is required, or may be accomplished by conversion of the manual action exerted upon said vacuum creating means into a catheter advancing action exerted upon said means for advancing the catheter. The above features are aimed at minimizing loss of needle tip engagement with blood vessel, while overpenetration is minimized by a specially configured needle catheter assembly favoring near parallel approach of the needle in respect to the blood vessel to penetrate.

27 Claims, 4 Drawing Sheets

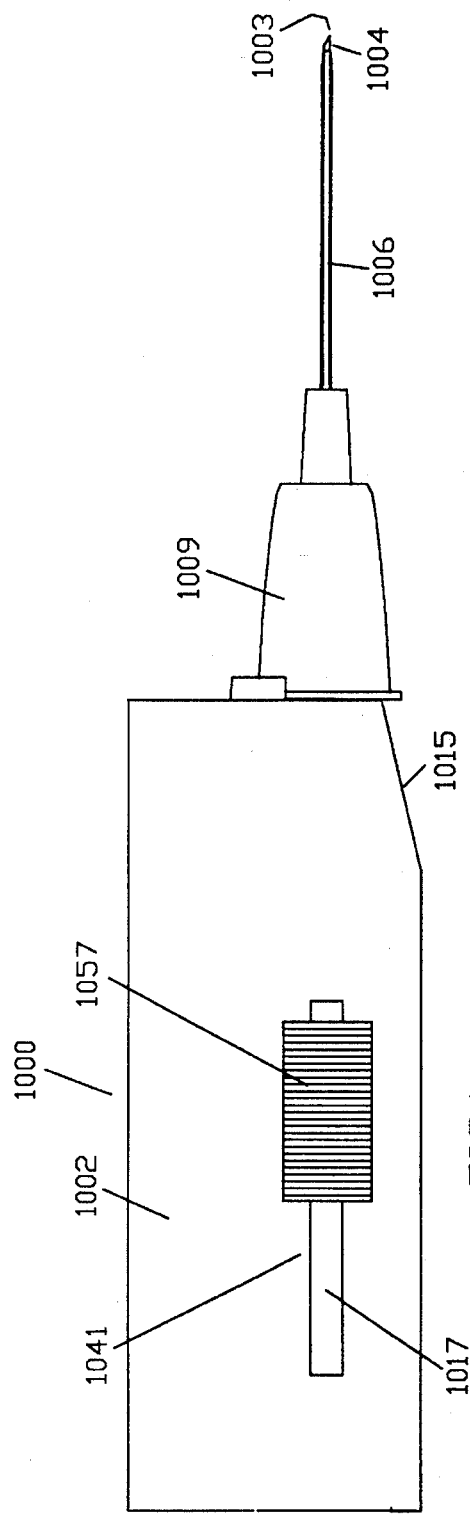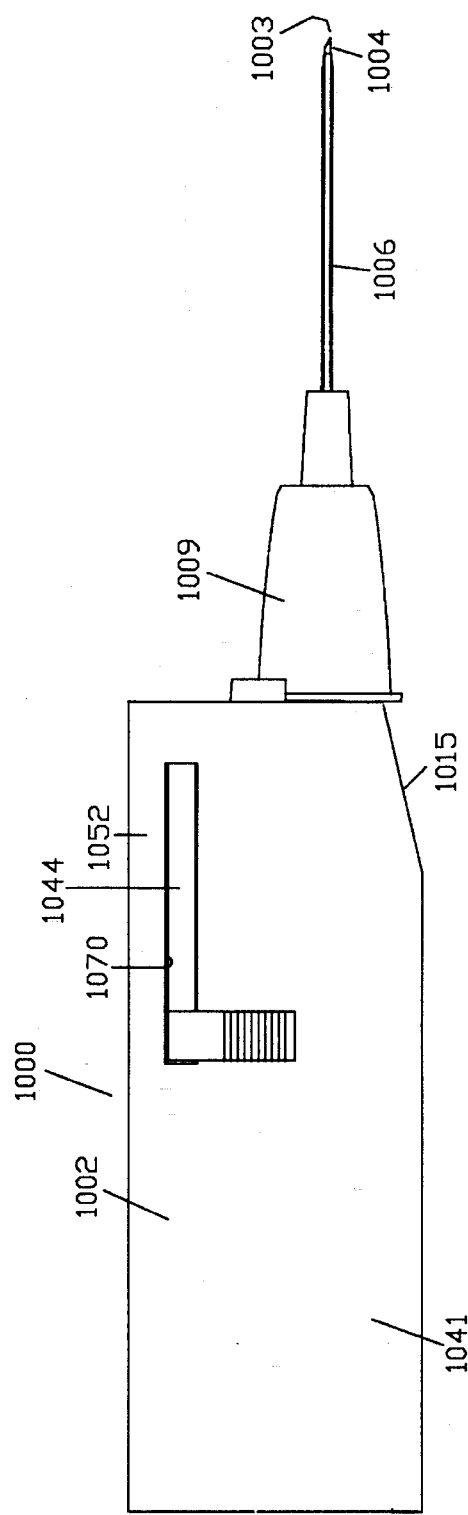

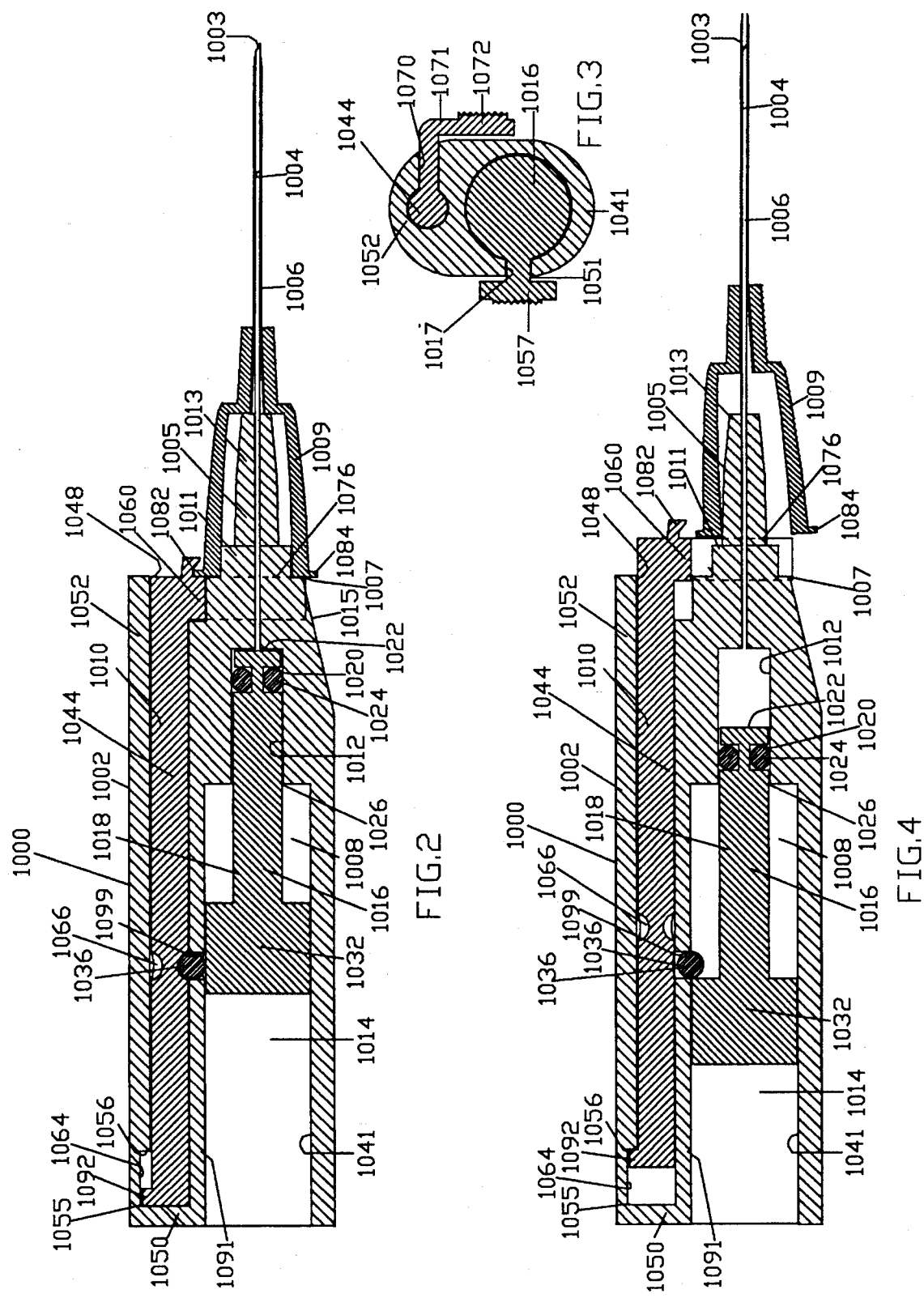

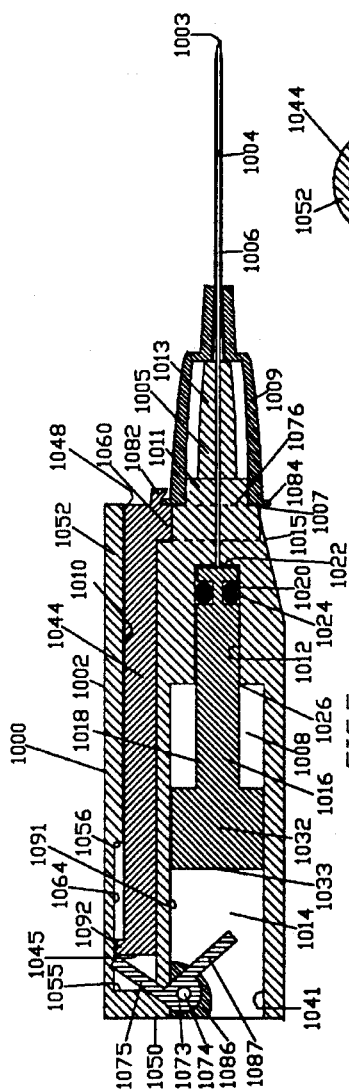
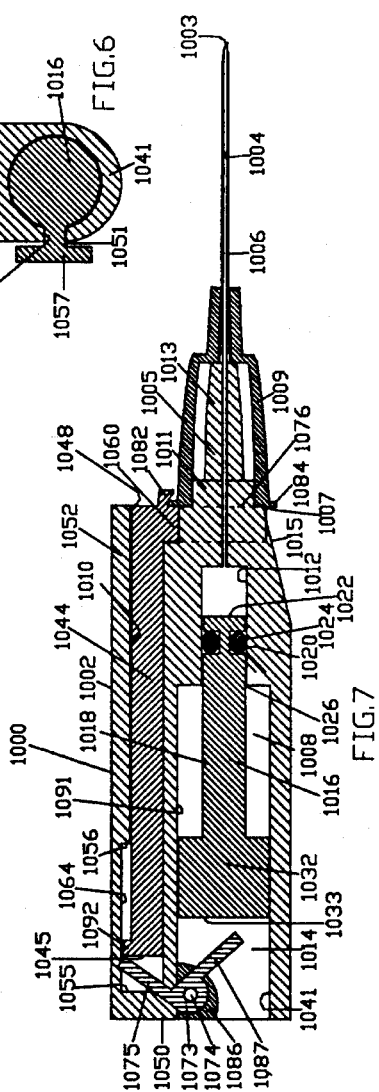
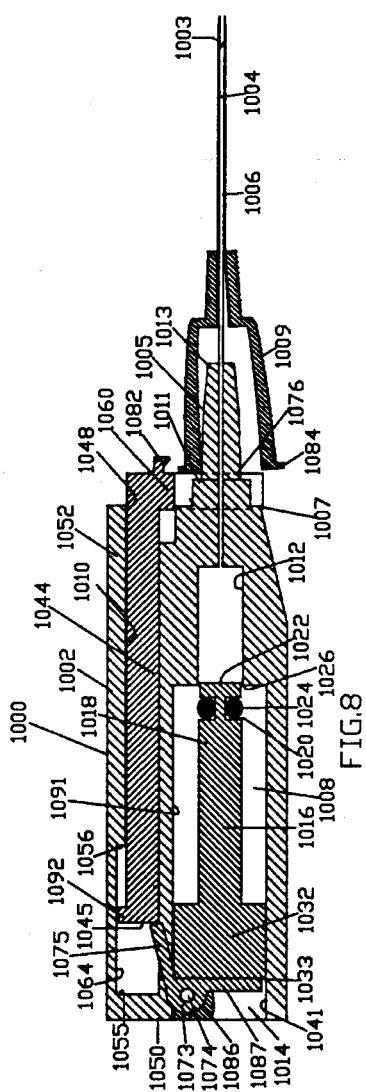
FIG.5  FIG.6  FIG.7  FIG.8

MANUAL CATHETER PLACEMENT DEVICE

BACKGROUND-FIELD OF THE INVENTION

This invention relates to manual catheter placement devices for the insertion of catheters into blood vessels.

BACKGROUND-DESCRIPTION OF THE PRIOR ART

Intravascular catheters are used to gain access into the vascular system for a variety of reasons: administration of drugs, blood, blood products, fluids, contrast media for diagnostic studies. The catheter design, since its inception, has remained basically the same: a tubular hollow flexible structure provided with a catheter hub, said catheter with its hub encircling and being slideable over a hollow needle and its hub. Catheter placement into vessel lumen is accomplished by the operator by inserting the needle tip into a blood vessel, ascertaining blood vessel penetration by visualization of the backflow of blood in the needle hub and by manually advancing the catheter into the vessel lumen by manually sliding it over the needle. Numerous are the reasons of failure in cannulating a blood vessel, the main being the failure by the operator in ascertaining blood vessel penetration by the needle tip. Failure of recognizing blood vessel penetration results in overpenetration of the blood vessel by the needle tip. Blood return through the hollow needle, up to the needle hub, is notoriously slow due to the fact the blood pressure within a vessel is notoriously low, particularly in the veins, and furthermore being needle I.D. and needle length dependent. To obviate this serious problem Zadini et al. describe an automatic cannulation device and a semiautomatic cannulation device in which backflow of blood is accelerated by vacuum means respectively in U.S. Pat. No. 5,312,361 and Divisional application No. 08/162,457 of said patent. In both patents the catheter is advanced into a vessel lumen by self propelling means such as a spring once the blood vessel is penetrated and said catheter advancement can be respectively automatically or manually triggered. In U.S. Pat. No. 4,464,171 by M. J. Garwin, No. 4,464,177 by J. McGaughey et Al., No. 4,904, 240 by R. L. Hoover, backflow of blood is accelerated, however the operation resulting in advancement of the catheter into a blood vessel is a multistep process lacking continuity and requiring change of position of one hand or the use of two hands. The operator, after accelerating backflow of blood by manual means and ascertaining occurred penetration by visualization of blood return must position his or her finger on the catheter hub or, as in the cited Garvey patent, on a "slide arm" in order to advance the catheter into the penetrated vessel. The operation is a multistep process, lacking continuity, requiring changing of hand position or use of two hands, due to the fact that the manual operation to accelerate backflow of blood is a distinct process requiting different handling from the manual operation of advancing the catheter: no mechanism connects or mediates the two process. Such a multistep process results in frequent loss of engagement of the needle tip from the penetrated vessel, with consequent failure of cannulation. The engagement of the needle tip in the vessel and its maintenance in this position is the most critical factor in a successful blood vessel cannulation.

BRIEF SUMMARY AND OBJECT OF INVENTION

The disadvantage of manually placing a catheter into a blood vessel are overcome with the present invention and an improved manual catheter placement device is proposed which permits blood vessel cannulation as a continuous process with smooth operation, wherein the means for accelerating the backflow of blood actuates the means for manual advancement of the catheter. The advantage of the present invention are preferably attained by providing an improved manual catheter placement device comprising a needle, a catheter concentric with the needle, manual means of accelerating backflow of blood, means for manually advancing the catheter and means for actuating said manually advancing means connecting the two processes, conferring a continuity of operation to the device, a smooth, easy one handed operation, which results in minimizing the risk of losing needle tip engagement with the penetrated blood vessel. Another object of the present invention is to provide an improved manual catheter placement device which facilitate insertion and placement of the catheter, by providing the device with catheter needle assembly specifically designed to enter a vessel with a near parallel approach in order to minimize risk of overpenetration of blood vessel.

DRAWING FIGURES

FIGS. 1 and 1A are side views of the manual catheter placement device.

FIG. 2 is a cross sectional view of the catheter placement device at rest, prior to use.

FIG. 3 is cross sectional view of the device of FIG. 1.

FIG. 4 is cross sectional view of the device of FIG. 1 shown in use, after penetration of a blood vessel.

FIG. 5 is a cross sectional view of an alternative form of the device of FIG. 1, at rest prior to use.

FIG. 6 is a cross sectional view of the device of FIG. 5.

FIG. 7 is across sectional of the device of FIG. 5, shown in a stage after skin penetration but prior to blood vessel penetration.

FIG. 8 is a cross sectional view of the device of FIG. 5 shown after blood vessel penetration.

DETAILED DESCRIPTION OF THE INVENTION

Figure 9:
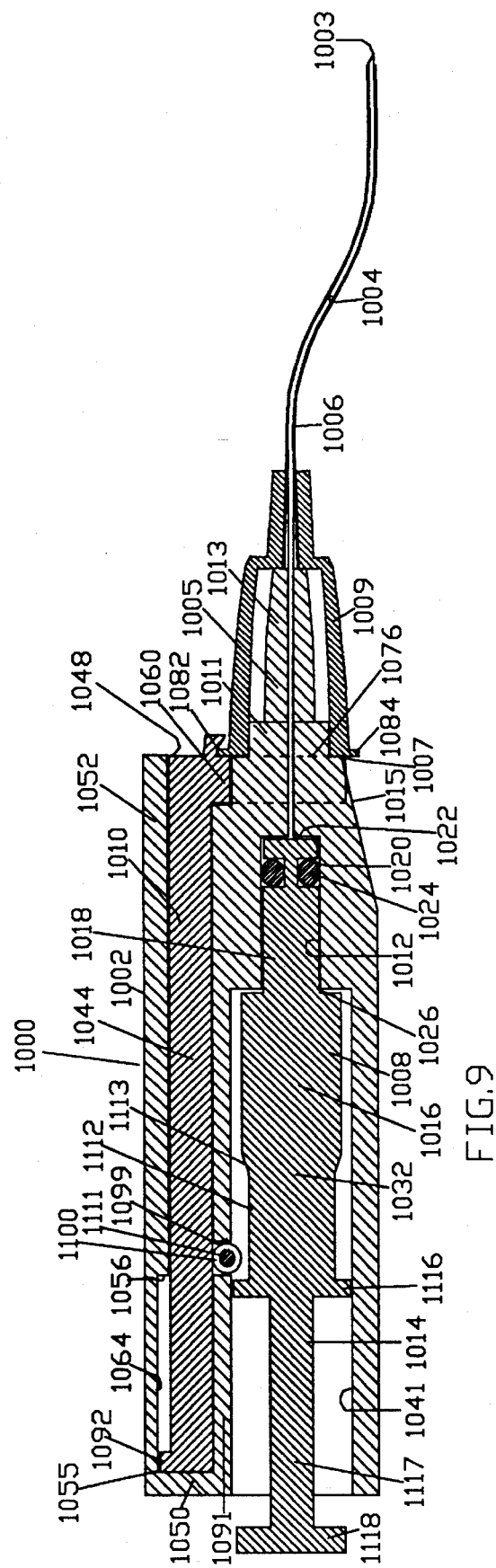
FIG. 9 is across sectional view of an alternative form of the device of FIG. 1.

A typical embodiment of the Catheter Placement is illustrated in FIGS. 1 to 4. FIG. 1 is a side view of the device, generally indicated at 1, prior to use. The device is composed of three main parts: a housing 2, a needle 1004 and a catheter 1006. FIG. 2 is a cross-sectional view of the device of FIG. 1. Housing 1002 is composed of two parallel chambers of generally cylindrical shape: piston chamber 1008 and intermediate member chamber 1010, separated longitudinally by divider wall 1091. Piston chamber 1008 delimited laterally by sidewall 1041, is composed of an anterior or vacuum chamber 1012 in communication with hollow needle 1004 and posterior chamber 1014 of larger diameter than vacuum chamber 1012. In one embodiment side wall 1041 of vacuum chamber 1008 should permit visualization of the interior of the chamber, for instance by being made of transparent material. Posterior chamber 1014 is in continuity with vacuum chamber 1012 via opening 1026. Posterior chamber 1014 is open posteriorly and is separated from intermediate member chamber by divider wall 1091 as above described. In piston chamber 1008 piston 1016 is slideably mounted. Piston 1016 is composed of two segments: an anterior segment 1018, which, prior to use, is in a fully advanced position within chamber 1012, and posterior piston segment 1032 of larger diameter, contained in posterior piston chamber 1014. The anterior piston segment 1018 of piston 1016 has annular groove 1020 formed in proximity of its front piston segment 1022, where 0-ring 1024 is mounted in airtight and slideable fashion within side walls 1041 of piston chamber 1012. Posterior piston segment 1032, in continuity with anterior piston segment 1018 is slideably mounted in posterior chamber 1014. As shown in FIGS. 1 and 3, side wall 1041 of piston chamber 1008 has a lateral slit 1017 for arm 1051 of side piston handle 1057 connected via said arm 1051 to piston 1016. Slit 1017 permits the sliding of the piston 1016 by the operator acting upon said side piston handle 1057 as it will be described in the operation. Piston 1016 may also be designed as a piston plunger such as a syringe plunger wherein the operator withdraws the piston by pulling back the plunger. However, the described piston version 1016 with side handle 1057 is preferable, being designed to render manual withdrawal of piston 1016 via displacement of side handle 1057 an easy and convenient operation for the operator's hand holding the device, averting the use of two hands, which is likely to occur in the mentioned version with the plunger. Intermediate member chamber 1010 of generally cylindrical shape delimited laterally by side wall 1052, is open anteriorly via opening 1048 and closed posteriorly by posterior wall 1050. Within chamber 1010 is slideably mounted intermediate member 1044. Side wall 1052 of intermediate member chamber 1010 is formed superiorly in its proximal segment with longitudinal groove 1064 for engagement with tooth 1092 of intermediate member 1044, said groove 1064 extending from posterior end 1055 up to arrest 1056 anteriorly. As shown in FIGS. 1A and 3, side wall 1052 of intermediate member chamber 1010 is also formed with lateral slit 1070 for arm 1071 of handle 1072 of intermediate member 1044 connected via said arm 1071 to intermediate member 1044. Slit 1070 permits the sliding of intermediate member 1044 by the operator acting upon said handle 1072 as it will be explained below in the description of the operation. Intermediate member 1044 of general cylindrical shape to slideably fit chamber 1010, has from portion or plate 1060. Intermediate member 1044, is also formed with annular recess 1066 for ball member 1036. Front portion or plate 1060 of intermediate member 1044, has opening 1076 to accommodate needle hub 1005 and has hook 1082 to releasably engage flange 1084 of catheter hub 1009. Window 1099 is formed in divider wall 1091 between intermediate member chamber 1010 and piston chamber 1008 to house ball member 1036. As shown in FIG. 2, with device 1000 in position of rest, prior to use, ball member 1036 is shown engaged in window 1099 of divider wall 1091, seating inferiorly on side wall of piston 1016 and superiorly, locking intermediate member 1044 by engaging correspondent annular recess 1066 of intermediate member 1044. Piston 1016 interfaces with intermediate member 1044 via ball member 1036 and window 1099. Needle hub 1005 protrudes from anterior end 1007 of housing 1002. Needle hub 1005 has base 1011 which precisely fits within catheter hub 1009 of catheter 1006 and has nozzle 1013 in continuity with needle hub base 1011 to allow adequate radial leeway for release of catheter hub 1009 of catheter 1006 from hook 1082 of plate 1060 of intermediate member 1044, when catheter 1006 is advanced, as it will be described in the description of the operation. Housing 1002 has a slant 1015 in its antero-inferior segment to facilitate the direction of insertion of needle 1004 into a vessel lumen. Hollow needle 1004 has tip 1003 and protrudes from needle hub 1005 previously described. Catheter 1006 and catheter hub 1009 are slideably mounted respectively over needle 1004 and needle hub 1005. Catheter hub 1009 has flange 1084 releasably engaged with hook 1082 of plate 1060.

The device is operated as follows: the operator with the device in his or her hands penetrates the skin of a patient with needle tip 1003. As soon as needle tip 1003 is well under the skin, the operator will act upon handle 1057 of piston 1016 by sliding it posteriorly. He or she could use any finger of the operating hand. Posterior displacement of piston 1016 will create a vacuum in front of piston 1016. However posterior displacement of piston 1016 will be limited, due to the sealing of needle tip 1003 caused by the patient tissues above the vessel, as the Operator senses sufficient resistance by the vacuum being created in front anterior piston segment 1018 of piston 1016. As soon as needle tip 1003 penetrates a blood vessel, blood backflow will be accelerated, rushing into vacuum chamber 1012. The accelerated backflow of blood will permit an almost immediate visualization of blood by the operator upon penetration of the blood vessel. Upon such visualization of backflow of blood, the operator will further displace posteriorly piston 1016 acting on handle 1057. Simultaneously the operator will displace anteriorly intermediate member 1044 via acting on handle 1072 with another finger of the same hand in a way that, while piston 1018 is displaced posteriorly simultaneously intermediate member 1044 is being displaced anteriorly. Such anterior displacement of intermediate member 1044 is permitted as a result of the release of locking ball 1036 from recess 1066 of intermediate member 1044 occurring with the withdrawal of piston 1016.

Anterior manual displacement of intermediate member 1044 will result in advancement of catheter 1006 into the blood vessel.

The manual posterior displacement of piston 1016 resulting in unlocking of intermediate member 1044 add permitting its manual advancement, may however be also actuated by the operator sensing the fall of resistance to the continuous withdrawing force applied by the operator upon said piston via said piston handle 1057, said fall of resistance occurrs upon blood vessel penetration. Hook 1082 will continue to engage with flange 1084 of catheter hub 1009 for a predetermined amount of advancement of intermediate member 1044 and precisely until catheter hub 1009 slides completely over base 1011 of needle hub 1005. In fact needle hub base 1011 by fitting exactly within catheter hub 1009 prevents radial leeway and consequent disengagement of flange 1084 of catheter hub 1009 from hook 1082 of arm or plate 1072. When catheter hub 1009 is advanced over nozzle 1013 of needle hub 1005 adequate radial leeway is allowed to catheter hub 1009 by needle nozzle 1013 of smaller diameter than needle base 1011. Radial leeway of catheter hub 1006 in respect of needle nozzle 1011 will permit disengagement of catheter hub 1006 from hook 1082 of plate 1060 of propelling unit 1002. The catheter 1006 will be free to be advanced further into the vessel lumen by the operator up to the desired length.

FIGS. 5 to 8 describes an alternative form of the device of FIGS. 1 to 4. The device is basically the same as the one described in FIGS. 1 to 4 except for few differences outlined below. Ball 1036, recess 1066, window 1099, intermediate member chamber slit 1070, intermediate member handle 1072 with its arm 1071 are no longer present. Interface menas or engagement means or lever 1073 is positioned posteriorly to piston 1016 and intermediate member 1044, mounted in bracket 1086 of divider wall 1091 via pin 1074. In position of rest, lower arm 1087 of lever 1073 is spaced a predetermined amount from posterior face 1033 of posterior piston segment 1032 &piston 1016 while upper arm 1075 is near contact or contact with posterior face 1045 of intermediate member 1044.

In use the device is operated as the device of FIGS. 1 to 4. Posterior piston segment 1032 of piston 1016, displaced posteriorly manually by the operator acting upon handle 1057 will propel forward intermediate member 1044 resulting in advancement of catheter 1006 into a blood vessel via tilting of lever 1073.

FIG. 9 shows an alternate form of the device of FIGS. 1 to 4. In this form propelling of intermediate member 1044 is accomplished via the interposition of interface means or engagement means or friction roller 1100 positioned between intermediate member 1044 and piston 1016. The device is basically the same as the one described in FIGS. 1 to 4 except that ball 1036, recess 1066, window 1099, intermediate member chamber slit 1070, intermediate member handle 1072 with its arm 1071 are no longer present. Friction roller 1100 is positioned between intermediate member 1044 and piston 1016, friction roller 1110 being mounted in seating 1099 of divider wall 1091 via center pin 1111. Friction roller 1100 can be substituted by a toothed wheel or gear engaging corresponding toothed racks in both piston 1016 and intermediate member 1044. Posterior piston segment 1032 of piston 1016 has proximal segment 1112 of smaller diameter in order to delay purposely friction engagement of piston 1016 with roller 1100 up to piston slant 1113. The device is operated as the previously described devices. In this version piston 1016 displaced posteriorly manually by the operator acting upon handle 1118 of piston plunger 1117, will propel forward intermediate member 1044 resulting in advancement of catheter 1006 into a blood vessel. Forward propelling of intermediate member 1044 will be accomplished by the rotation of roller 1100 caused by the manual backward displacement of posterior piston segment 1032 of piston 1116. In fact, while piston member 1016 is manually displaced posteriorly by the operator, intermediate member 1044 will be displaced in the opposite direction i.e. forwardly, resulting. as above described, in advancement of catheter 1006 into a blood vessel. Hollow needle 1004 can be shaped as shown in FIG. 9 in a generally "S" or "bayonet" shaped fashion in order to facilitate its insertion into a vessel by providing the manual catheter placement device with a near parallel approach to a vessel. Same goal can be achieved by constructing the needle hub at an angle less than 180 degree in respect of the longitudinal axis of the device.

Obviously, numerous other variations and modifications can be made without departing from the spirit of the present invention. Therefore, it should be clearly understood that the forms of the present invention described above and shown in the figures of the accompanying drawing are illustrative only and are not intended to limit the scope of the present invention.

What we claim is:

1. An intravascular catheter placement device for operator insertion of an intravascular catheter into the interior of a blood vessel, comprising:
   (a) an intravascular catheter;
   (b) a hollow needle, the catheter being concentric to and over the needle;
   (c) a vacuum chamber in flow communication with the hollow needle; and
   (d) means for creating a vacuum within the vacuum chamber, said means for creating vacuum being manually displaceable upon blood vessel penetration by said needle to enable a manually driven advancement of said catheter.

2. The device of claim 1 further comprising:
   locking means releasably retaining said catheter over the needle, said locking means being releasable in response to a manual displacement of said manually displaceable means for creating vacuum upon blood vessel penetration by said needle, so as to enable said manually driven advancement of said catheter.

3. The device of claim 2 wherein said releasable locking means retains said catheter over the needle via an intermediate member releasably engaged to said catheter, and the catheter is advanced by a manual advancement of said intermediate member, said intermediate member having means for being manually advanced.

4. The device of claim 2 wherein said manual displacement of said vacuum creating means is a rearward manual displacement.

5. The device of claim 2 wherein said vacuum creating means comprises a piston slidable within said vacuum chamber, and rearwardly displaceable.

6. The device of claim 5 wherein said piston has a grippable handle extending outwardly from the device for manual displacement of said piston.

7. The device of claim 6 wherein the piston is manually withdrawable via said grippable handle to create a vacuum in the chamber, and, upon blood vessel penetration by said needle, is further rearwardly displaceable with minimal resistance due to vacuum loss.

8. The device of claim 1 further comprising:
   engagement means for engaging said vacuum creating means with said catheter upon blood vessel penetration by said needle, and converting a manual displacement of said manually displaceable means for creating vacuum into said catheter advancement.

9. The device of claim 8 wherein said engagement means engages the vacuum creating means with the catheter via an intermediate member releasably engaged to said catheter, and the catheter is advanced by advancement of said intermediate member which in turn is advanced by manual displacement of said vacuum creating means.

10. The device of claim 8 wherein said manually displaceable means for creating vacuum is rearwardly displaceable.

11. The device of claim 8 wherein the means for creating a vacuum comprises a piston slidable within the vacuum chamber, and rearwardly displaceable.

12. The device of claim 11 wherein said piston has a grippable handle extending outwardly from the device for manual displacement of said piston.

13. The device of claim 12 wherein the piston is manually withdrawable via said grippable handle to create a vacuum in the chamber, and, upon blood vessel penetration by said needle, is further rearwardly displaceable with minimal resistance due to vacuum loss.

14. The device of claim 10 wherein said engaging means comprises a pivotally mounted lever means having an arm being contacted and moved by said manual rearwardly displaceable means for creating vacuum, and another arm engaging said catheter to convert the rearward displacement of said vacuum creating means into said catheter advancement.

15. The device of claim 10 wherein said engaging means comprises a gear to convert the rearward displacement of the vacuum creating means into said catheter advancement.

16. The device of claim 10 wherein said engaging means comprises a friction roller to convert the rearward displacement of the vacuum creating means into said catheter advancement.

17. The device of claim 10 wherein said engaging means comprises a coupling means to couple said vacuum creating means with said catheter to convert the rearward displacement of the vacuum creating means into said catheter advancement.

18. The device of claim 1 wherein, to facilitate insertion of said intravascular catheter into the blood vessel and minimize blood vessel overpenetration by the needle, the needle has a tip segment having a longitudinal axis adjusted to near a parallel approach to a longitudinal axis of the vessel.

19. The device of claim 18, wherein said tip segment longitudinal axis has two contiguous curvatures facing opposite directions.

20. The device of claim 18, wherein said tip segment longitudinal axis has generally a bayonet type of shape.

21. The device of claim 18, wherein said tip segment longitudinal axis is at an angle less than 180 degrees in respect to a longitudinal axis of a contiguous needle segment.

22. The device of claim 18, wherein a longitudinal axis of said needle is at an angle less than 180 degrees in respect to a longitudinal axis of a needle hub connected to said needle.

23. The device of claim 18, wherein said needle is connected to a needle hub, said needle hub having a longitudinal axis at an angle less than 180 degrees in respect to a longitudinal axis of said device connected to said needle hub.

24. The device of claim 18, wherein said needle tip segment is eccentric in respect to a needle hub connected to said needle.

25. An intravascular catheter placement device for insertion of an intravascular catheter into the interior of a blood vessel comprising:

(a) an intravascular catheter;
(b) a hollow needle, said catheter being concentric to said hollow needle;
(c) means for advancing said catheter, said means for advancing said catheter releasably engaging said catheter to retain said catheter in a retracted position in respect to said needle upon withdrawal of said needle, and to release said catheter upon advancement of said catheter to an advanced position in respect to said needle.

26. An intravascular catheter placement device for insertion of an intravascular catheter into the interior of a blood vessel comprising:

(a) an intravascular catheter;
(b) a hollow needle, said catheter being concentric to said hollow needle;
(c) means for accelerating backflow of blood upon blood vessel penetration by said needle, said means for accelerating backflow of blood being manually displaceable to enable a manually driven advancement of said catheter upon said blood vessel penetration.

27. An intravascular catheter placement device for insertion of an intravascular catheter into the interior of a blood vessel comprising:

(a) an intravascular catheter;
(b) a hollow needle, said catheter being concentric to and over said hollow needle;
(c) a vacuum chamber communicating with said hollow needle;
(d) means for creating vacuum within said vacuum chamber, said vacuum creating means actuating manual advancement of the catheter upon blood vessel penetration by said needle.

* * * * *